United States Patent
Miller et al.

(10) Patent No.: US 8,814,025 B2
(45) Date of Patent: Aug. 26, 2014

(54) FIBRIN PAD MATRIX WITH SUSPENDED HEAT ACTIVATED BEADS OF ADHESIVE

(75) Inventors: Matthew C. Miller, Cincinnati, OH (US); Yi-Lan Wang, Bell Mead, NJ (US); Israel Nur, Moshav Timmorim (IL); Aron O. Zingman, Cambridge, MA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 222 days.

(21) Appl. No.: 13/233,633

(22) Filed: Sep. 15, 2011

(65) Prior Publication Data
US 2013/0068820 A1    Mar. 21, 2013

(51) Int. Cl.
*A61B 17/068*    (2006.01)
*A61B 17/00*    (2006.01)
*A61B 17/072*    (2006.01)
*A61B 17/29*    (2006.01)

(52) U.S. Cl.
CPC ..... *A61B 17/07207* (2013.01); *A61B 17/00491* (2013.01); *A61B 2017/005* (2013.01); *A61B 2017/2929* (2013.01); *A61B 17/07292* (2013.01)
USPC ....... 227/180.1; 227/19; 227/176.1; 606/151; 606/153; 606/219

(58) Field of Classification Search
USPC .............. 227/19, 175.1, 176.1, 179.1, 180.1; 606/139, 213, 219, 229, 151, 153
See application file for complete search history.

(56) References Cited

U.S. PATENT DOCUMENTS

| 2,303,131 | A | 11/1942 | Morgan |
| 3,364,200 | A | 1/1968 | Ashton et al. |
| 3,496,940 | A | 2/1970 | Steinman |
| 3,526,228 | A | 9/1970 | Lyng |
| 4,222,383 | A | 9/1980 | Schossow |
| 4,513,746 | A | 4/1985 | Aranyi et al. |
| 4,549,545 | A | 10/1985 | Levy |

(Continued)

FOREIGN PATENT DOCUMENTS

| CA | 481943 | 2/1947 |
| EP | 328 401 | 8/1989 |

(Continued)

OTHER PUBLICATIONS

Abstract for FR2789885.

(Continued)

*Primary Examiner* — Scott A. Smith
(74) *Attorney, Agent, or Firm* — Frost Brown Todd LLC (57) ABSTRACT

A surgical instrument includes a handle portion, a shaft housing a firing bar, an end effector comprising an anvil, a lower jaw, and a stapling and severing assembly responsive to a longitudinal closing motion produced by the handle portion and the shaft. The lower jaw is configured to receive a cartridge when in an open position. The cartridge includes a housing, a plurality of staples disposed in the housing, and a deck disposed over the plurality of staples. The deck defines apertures, with each aperture being substantially disposed over each staple. The cartridge further receives a matrix including glue beads suspended in the matrix. The staples are driven through the matrix to secure the matrix to tissue. The glue beads are activated when the matrix is secured to the tissue, such that the activated adhesive further secures the staple line in the tissue.

20 Claims, 9 Drawing Sheets

(56) References Cited

U.S. PATENT DOCUMENTS

| | | | |
|---|---|---|---|
| 4,610,250 | A | 9/1986 | Green |
| 4,693,720 | A | 9/1987 | Scharnberg et al. |
| 4,805,823 | A | 2/1989 | Rothfuss |
| 5,011,493 | A | 4/1991 | Belykh et al. |
| 5,064,057 | A | 11/1991 | Iwatsuki et al. |
| 5,263,629 | A | 11/1993 | Trumbull et al. |
| 5,282,829 | A | 2/1994 | Hermes |
| 5,297,324 | A | 3/1994 | Su |
| 5,327,914 | A | 7/1994 | Shlain |
| 5,366,480 | A | 11/1994 | Corriveau et al. |
| 5,383,904 | A | 1/1995 | Totakura et al. |
| 5,393,594 | A | 2/1995 | Koyfman et al. |
| 5,411,193 | A | 5/1995 | Culp |
| 5,415,334 | A | 5/1995 | Williamson, IV et al. |
| 5,465,895 | A | 11/1995 | Knodel et al. |
| 5,466,462 | A | 11/1995 | Rosenthal et al. |
| 5,496,603 | A | 3/1996 | Riedel et al. |
| 5,503,638 | A | 4/1996 | Cooper et al. |
| 5,542,594 | A | 8/1996 | McKean et al. |
| 5,565,210 | A | 10/1996 | Rosenthal et al. |
| 5,597,107 | A | 1/1997 | Knodel et al. |
| 5,607,590 | A | 3/1997 | Simizu |
| 5,607,686 | A | 3/1997 | Totakura et al. |
| 5,632,432 | A | 5/1997 | Schulze et al. |
| 5,639,851 | A | 6/1997 | Bezwada et al. |
| 5,641,566 | A | 6/1997 | Kranzler et al. |
| 5,644,002 | A | 7/1997 | Cooper et al. |
| 5,673,840 | A | 10/1997 | Schulze et al. |
| 5,690,675 | A | 11/1997 | Sawyer et al. |
| 5,704,534 | A | 1/1998 | Huitema et al. |
| 5,711,958 | A | 1/1998 | Cohn et al. |
| 5,733,308 | A | 3/1998 | Daugherty et al. |
| 5,749,968 | A | 5/1998 | Melanson et al. |
| 5,752,965 | A | 5/1998 | Francis et al. |
| 5,755,778 | A | 5/1998 | Kleshinski |
| 5,766,188 | A | 6/1998 | Igaki |
| 5,769,892 | A | 6/1998 | Kingwell |
| 5,810,855 | A | 9/1998 | Rayburn et al. |
| 5,814,055 | A | 9/1998 | Knodel et al. |
| 5,814,057 | A | 9/1998 | Oi et al. |
| 5,843,096 | A | 12/1998 | Igaki et al. |
| 5,902,312 | A | 5/1999 | Frater et al. |
| 5,997,895 | A | 12/1999 | Narotam et al. |
| 6,019,791 | A | 2/2000 | Wood |
| 6,031,148 | A | 2/2000 | Hayes et al. |
| 6,099,551 | A | 8/2000 | Gabbay |
| 6,174,333 | B1 | 1/2001 | Kadiyala et al. |
| 6,203,564 | B1 | 3/2001 | Hutton et al. |
| 6,245,081 | B1 | 6/2001 | Bowman et al. |
| 6,273,897 | B1 | 8/2001 | Dalessandro et al. |
| 6,277,397 | B1 | 8/2001 | Shimizu |
| 6,312,474 | B1 | 11/2001 | Francis et al. |
| 6,325,810 | B1 | 12/2001 | Hamilton et al. |
| 6,355,699 | B1 | 3/2002 | Vyakarnam et al. |
| 6,488,197 | B1 | 12/2002 | Whitman |
| 6,495,127 | B1 | 12/2002 | Wallace et al. |
| 6,503,257 | B2* | 1/2003 | Grant et al. ............ 606/151 |
| 6,511,748 | B1 | 1/2003 | Barrows |
| 6,514,283 | B2* | 2/2003 | DiMatteo et al. ............ 623/1.13 |
| 6,592,597 | B2 | 7/2003 | Grant et al. |
| 6,638,285 | B2 | 10/2003 | Gabbay |
| 6,656,193 | B2 | 12/2003 | Grant et al. |
| 6,704,210 | B1 | 3/2004 | Myers |
| 6,814,741 | B2 | 11/2004 | Bowman et al. |
| 6,835,336 | B2 | 12/2004 | Watt |
| 6,921,412 | B1 | 7/2005 | Black et al. |
| 6,962,594 | B1 | 11/2005 | Thevenet |
| 6,964,363 | B2 | 11/2005 | Wales et al. |
| 6,978,921 | B2 | 12/2005 | Shelton, IV et al. |
| 6,988,649 | B2 | 1/2006 | Shelton, IV et al. |
| 7,000,818 | B2 | 2/2006 | Shelton, IV et al. |
| 7,048,755 | B2 | 5/2006 | Bonutti et al. |
| 7,084,082 | B1 | 8/2006 | Shimizu |
| 7,111,769 | B2 | 9/2006 | Wales et al. |
| 7,143,923 | B2 | 12/2006 | Shelton, IV et al. |
| 7,147,138 | B2 | 12/2006 | Shelton, IV |
| 7,207,471 | B2 | 4/2007 | Heinrich et al. |
| 7,211,093 | B2 | 5/2007 | Sauer et al. |
| 7,268,205 | B2 | 9/2007 | Williams et al. |
| 7,303,108 | B2 | 12/2007 | Shelton, IV |
| 7,335,212 | B2 | 2/2008 | Edoga et al. |
| 7,367,485 | B2 | 5/2008 | Shelton, IV et al. |
| 7,377,928 | B2 | 5/2008 | Zubik et al. |
| 7,380,695 | B2 | 6/2008 | Doll et al. |
| 7,380,696 | B2 | 6/2008 | Shelton, IV et al. |
| 7,404,508 | B2 | 7/2008 | Smith et al. |
| 7,434,715 | B2 | 10/2008 | Shelton, IV et al. |
| 7,455,208 | B2 | 11/2008 | Wales et al. |
| 7,517,356 | B2 | 4/2009 | Heinrich |
| 7,607,557 | B2 | 10/2009 | Shelton, IV et al. |
| 7,708,180 | B2* | 5/2010 | Murray et al. ............ 227/175.1 |
| 7,721,930 | B2 | 5/2010 | McKenna et al. |
| 7,738,971 | B2 | 6/2010 | Swayze et al. |
| 7,744,627 | B2* | 6/2010 | Orban et al. ............ 606/215 |
| 7,845,533 | B2 | 12/2010 | Marczyk et al. |
| 7,883,524 | B2* | 2/2011 | Chen ............ 606/191 |
| 7,914,543 | B2* | 3/2011 | Roth et al. ............ 606/153 |
| 7,938,307 | B2* | 5/2011 | Bettuchi ............ 227/179.1 |
| 8,062,330 | B2* | 11/2011 | Prommersberger et al. .. 606/215 |
| 8,123,767 | B2* | 2/2012 | Bauman et al. ............ 606/151 |
| 8,157,152 | B2* | 4/2012 | Holsten et al. ............ 227/176.1 |
| 8,419,755 | B2* | 4/2013 | Deem et al. ............ 606/153 |
| 2002/0165559 | A1 | 11/2002 | Grant et al. |
| 2003/0120284 | A1 | 6/2003 | Palacios et al. |
| 2003/0183671 | A1 | 10/2003 | Mooradian et al. |
| 2004/0093024 | A1 | 5/2004 | Lousararian et al. |
| 2004/0167572 | A1 | 8/2004 | Roth et al. |
| 2004/0254608 | A1 | 12/2004 | Huitema et al. |
| 2005/0042250 | A1 | 2/2005 | Damien et al. |
| 2005/0059996 | A1 | 3/2005 | Bauman et al. |
| 2005/0070929 | A1 | 3/2005 | Dalessandro et al. |
| 2005/0101834 | A1 | 5/2005 | Merade |
| 2005/0107810 | A1 | 5/2005 | Morales et al. |
| 2005/0145671 | A1 | 7/2005 | Viola |
| 2005/0154403 | A1 | 7/2005 | Sauer et al. |
| 2005/0245965 | A1 | 11/2005 | Orban, III et al. |
| 2005/0249772 | A1 | 11/2005 | Maliviya et al. |
| 2005/0251153 | A1 | 11/2005 | Sakamoto et al. |
| 2005/0283256 | A1 | 12/2005 | Sommerich et al. |
| 2005/0288767 | A1 | 12/2005 | Kujawski et al. |
| 2006/0004388 | A1 | 1/2006 | Whayne et al. |
| 2006/0047312 | A1 | 3/2006 | Olmo et al. |
| 2006/0093655 | A1 | 5/2006 | Bar et al. |
| 2006/0094318 | A1 | 5/2006 | Matsuda et al. |
| 2006/0135992 | A1 | 6/2006 | Bettuchi et al. |
| 2006/0173470 | A1 | 8/2006 | Oray et al. |
| 2006/0212069 | A1 | 9/2006 | Shelton, IV |
| 2006/0229672 | A1 | 10/2006 | Forsberg |
| 2006/0265006 | A1 | 11/2006 | White et al. |
| 2006/0265007 | A1 | 11/2006 | White et al. |
| 2007/0016227 | A1 | 1/2007 | de la Torre et al. |
| 2007/0034667 | A1 | 2/2007 | Holsten et al. |
| 2007/0034669 | A1 | 2/2007 | de la Torre et al. |
| 2007/0049953 | A2 | 3/2007 | Shimoji et al. |
| 2007/0060932 | A1 | 3/2007 | Stack et al. |
| 2007/0066981 | A1 | 3/2007 | Meagher |
| 2007/0112360 | A1 | 5/2007 | De Deyne et al. |
| 2007/0128243 | A1 | 6/2007 | Serafica et al. |
| 2007/0131732 | A1 | 6/2007 | Holsten et al. |
| 2007/0150002 | A1 | 6/2007 | Szabo et al. |
| 2007/0156140 | A1 | 7/2007 | Baily |
| 2007/0190108 | A1 | 8/2007 | Datta et al. |
| 2007/0207180 | A1 | 9/2007 | Tanihara et al. |
| 2007/0213522 | A1 | 9/2007 | Harris et al. |
| 2007/0219571 | A1 | 9/2007 | Balbierz et al. |
| 2007/0225642 | A1 | 9/2007 | Houser et al. |
| 2007/0243227 | A1 | 10/2007 | Gertner |
| 2007/0246505 | A1 | 10/2007 | Pace-Floridia et al. |
| 2007/0286892 | A1 | 12/2007 | Herzberg et al. |
| 2008/0039871 | A1 | 2/2008 | Wallace et al. |
| 2008/0077131 | A1 | 3/2008 | Yates |
| 2008/0078800 | A1 | 4/2008 | Hess et al. |
| 2008/0078801 | A1 | 4/2008 | Shelton, IV et al. |
| 2008/0078802 | A1 | 4/2008 | Hess et al. |

(56) References Cited

U.S. PATENT DOCUMENTS

| | | | |
|---|---|---|---|
| 2008/0078803 A1 | 4/2008 | Shelton, IV et al. |
| 2008/0078804 A1 | 4/2008 | Shelton, IV et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0081881 A1 | 4/2008 | Swetlin et al. |
| 2008/0082124 A1 | 4/2008 | Hess et al. |
| 2008/0082126 A1 | 4/2008 | Murray et al. |
| 2008/0110959 A1 | 5/2008 | Orban, III et al. |
| 2008/0114381 A1 | 5/2008 | Voegle et al. |
| 2008/0114385 A1 | 5/2008 | Byrum et al. |
| 2008/0114399 A1 | 5/2008 | Bonutti |
| 2008/0125812 A1 | 5/2008 | Zubik et al. |
| 2008/0128469 A1 | 6/2008 | Dalessandro et al. |
| 2008/0140115 A1 | 6/2008 | Stopek |
| 2008/0200949 A1 | 8/2008 | Hiles et al. |
| 2008/0314960 A1 | 12/2008 | Marczyk et al. |
| 2009/0001122 A1 | 1/2009 | Prommersberger et al. |
| 2009/0076510 A1 | 3/2009 | Bell et al. |
| 2009/0118747 A1 | 5/2009 | Bettuchi et al. |
| 2010/0016888 A1 | 1/2010 | Calabrese et al. |
| 2012/0187179 A1* | 7/2012 | Gleiman .................. 227/176.1 |

FOREIGN PATENT DOCUMENTS

| | | |
|---|---|---|
| EP | 0 667 119 | 8/1995 |
| EP | 0 781 564 | 7/1997 |
| EP | 0 818 470 | 1/1998 |
| EP | 1 098 024 | 5/2001 |
| EP | 1 229 841 | 8/2002 |
| EP | 1256317 | 11/2002 |
| EP | 1 494 596 | 1/2005 |
| EP | 1 621 141 | 2/2006 |
| EP | 1 647 286 | 4/2006 |
| EP | 1 759 640 | 3/2007 |
| EP | 1 836 974 | 9/2007 |
| EP | 2481359 | 8/2012 |
| FR | 2 789 885 | 8/2000 |
| FR | 2 850 281 | 7/2004 |
| GB | 222 954 | 10/1924 |
| GB | 493 459 | 10/1938 |
| GB | 913 218 | 12/1962 |
| JP | 107 2740 | 3/1989 |
| JP | 3146773 | 6/1991 |
| JP | 5076586 | 3/1993 |
| JP | 11309151 | 11/1999 |
| WO | WO 93/10731 | 6/1993 |
| WO | WO 98/38923 | 9/1998 |
| WO | WO 01/17446 | 3/2001 |
| WO | WO 02/09593 | 2/2002 |
| WO | WO 02/22184 | 3/2002 |
| WO | WO 03/094743 | 11/2003 |
| WO | WO 2004/060425 | 7/2004 |
| WO | WO 2006/081174 | 8/2006 |
| WO | WO 2006/106269 | 10/2006 |
| WO | WO 2007/067621 | 6/2007 |
| WO | WO 2008/057281 | 5/2008 |

OTHER PUBLICATIONS

Abstract for FR2850281.
Abstract for JP1072740.
Abstract for JP11309151.
Abstract for JP3146773.
Abstract for JP5076586.
International Search Report dated Dec. 4, 2012 for Application No. PCT/US2012/054407.

* cited by examiner

FIBRIN PAD MATRIX WITH SUSPENDED HEAT ACTIVATED BEADS OF ADHESIVE

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in: U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,964,363, entitled "Surgical Stapling Instrument having Articulation Joint Support Plates for Supporting a Firing Bar," issued Nov. 15, 2005; U.S. Pat. No. 6,978,921, entitled "Surgical Stapling Instrument Incorporating an E-Beam Firing Mechanism," issued Dec. 27, 2005; U.S. Pat. No. 6,988,649, entitled "Surgical Stapling Instrument Having a Spent Cartridge Lockout," issued Jan. 24, 2006; U.S. Pat. No. 7,000,818, entitled "Surgical Stapling Instrument Having Separate Distinct Closing and Firing Systems," issued Feb. 21, 2006; U.S. Pat. No. 7,111,769, entitled "Surgical Instrument Incorporating an Articulation Mechanism having Rotation about the Longitudinal Axis," issued Sep. 26, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument having Multistroke Firing with Opening Lockout," issued Oct. 14, 2008; U.S. Pat. No. 7,721,930, entitled "Disposable Cartridge with Adhesive for Use with a Stapling Device," issued May 25, 2010; and U.S. Pat. No. 7,455,208, entitled "Surgical Instrument with Articulating Shaft with Rigid Firing Bar Supports," issued Nov. 25, 2008. The disclosure of each of the above-cited U.S. patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

Figure 1A:
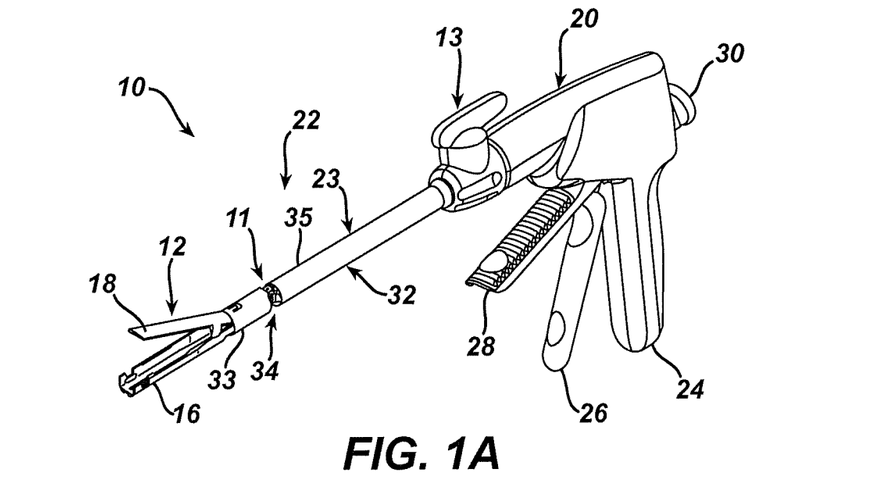
FIG. 1A depicts a perspective view of an articulating surgical instrument with an end effector in a nonarticulated position.
Figure 1B:
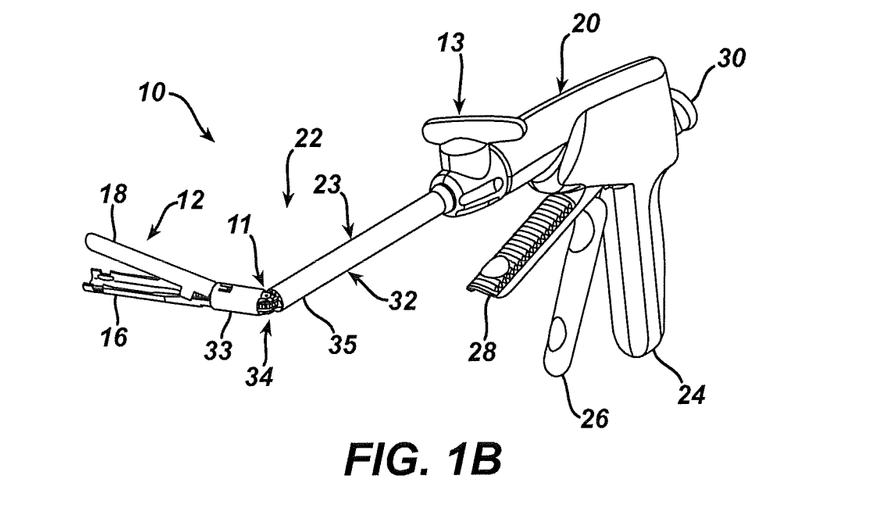
FIG. 1B depicts a perspective view of the surgical instrument of FIG. 1A with an end effector in an articulated position.

FIGS. 1-6 depict an exemplary surgical stapling and severing instrument (10) that is sized for insertion, in a nonarticulated state as depicted in FIG. 1A, through a trocar cannula passageway to a surgical site in a patient for performing a surgical procedure. Surgical and stapling and severing instrument (10) includes handle portion (20) connected to implement portion (22), the latter further comprising shaft (23) distally terminating in an articulating mechanism (11) and a distally attached end effector (12). Once articulation mechanism (11) and distally end effector (12) are inserted through the cannula passageway of a trocar, articulation mechanism (11) may be remotely articulated, as depicted in FIG. 1B, by articulation control (13). Thereby, end effector (12) may reach behind an organ or approach tissue from a desired angle or for other reasons. It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

End effector (12) of the present example includes a lower jaw (16) and a pivotable anvil (18). Handle portion (20) includes pistol grip (24) toward which closure trigger (26) is pivotally drawn by the clinician to cause clamping, or closing, of the anvil (18) toward lower jaw (16) of end effector (12). Such closing of anvil (18) is provided through an outmost closure sleeve (32), which longitudinally translates relative to handle portion (20) in response to pivoting of closure trigger (26) relative to pistol grip (24). A distal closure ring (33) of closure sleeve (32) is indirectly supported by frame (34) of implement portion (22). At articulation mechanism (11), a proximal closure tube (35) of closure sleeve (32) communicates with the distal portion (closure ring) (33). Frame (34) is flexibly attached to lower jaw (16) via articulation mechanism (11), enabling articulation in a single plane. Frame (34) also longitudinally slidingly supports a firing drive member (not shown) that extends through shaft (23) and communicates a firing motion from firing trigger (28) to firing bar (14). Firing trigger (28) is farther outboard of closure trigger (26) and is pivotally drawn by the clinician to cause the stapling and severing of clamped tissue in end effector (12), as will be described in greater detail below. Thereafter, release button (30) is depressed to release the tissue from end effector (12).

FIGS. 2-5 depict end effector (12) employing an E-beam firing bar (14) to perform a number of functions. As best seen in FIGS. 3A-3B, firing bar (14) includes a transversely oriented upper pin (38), a firing bar cap (44), a transversely oriented middle pin (46), and a distally presented cutting edge (48). Upper pin (38) is positioned and translatable within an anvil pocket (40) of anvil (18). Firing bar cap (44) slidably engages a lower surface of lower jaw (16) by having firing bar (14) extend through channel slot (45) (shown in FIG. 3B) that is formed through lower jaw (16). Middle pin (46) slidingly engages a top surface of lower jaw (16), cooperating with firing bar cap (44). Thereby, firing bar (14) affirmatively spaces end effector (12) during firing, overcoming pinching that may occur between anvil (18) and lower jaw (16) with a minimal amount of clamped tissue and overcoming staple malformation with an excessive amount of clamped tissue.

Figure 2:
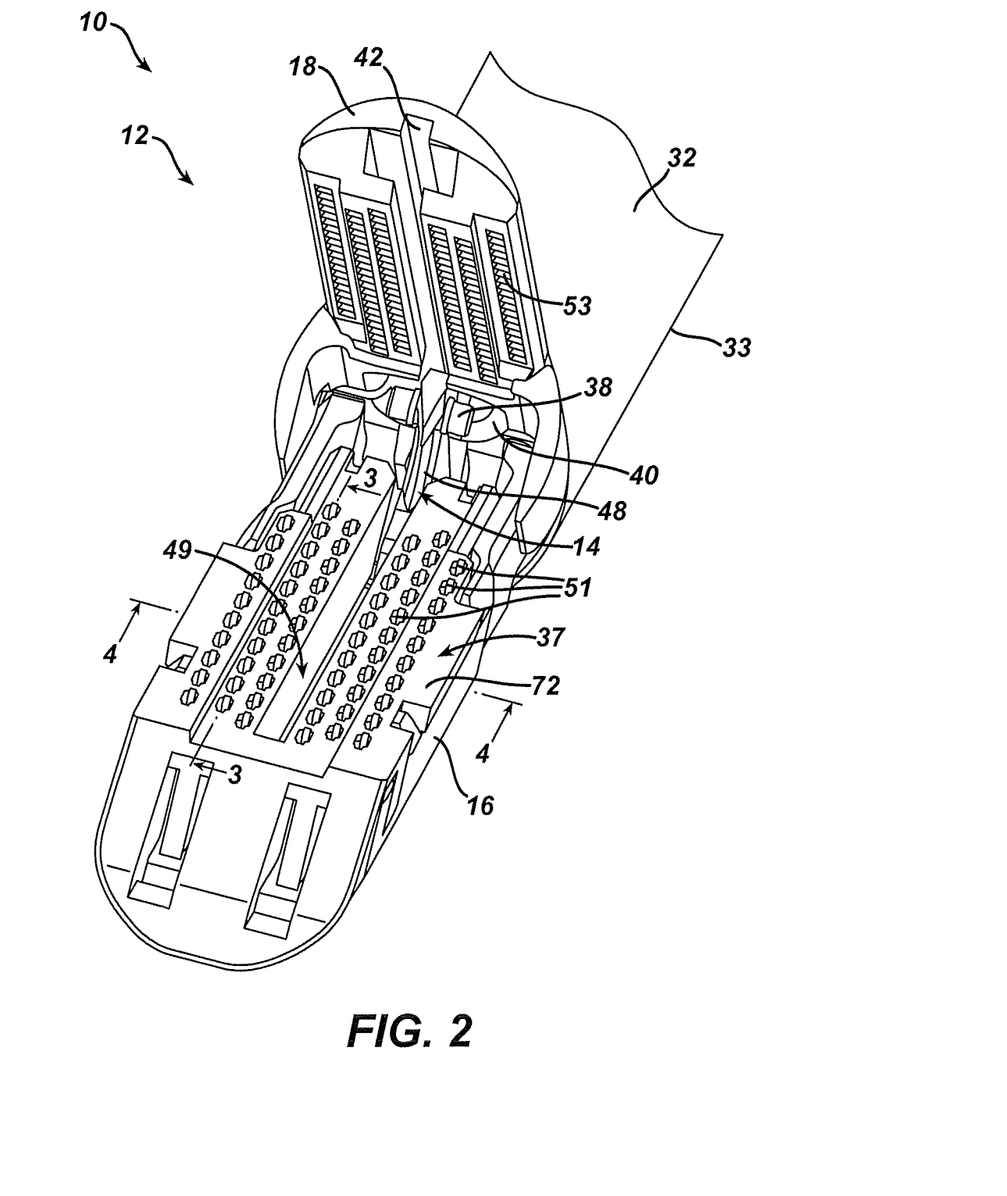
FIG. 2 depicts a perspective view of an opened end effector of the surgical instrument of FIGS. 1A-1B.
Figure 3A:
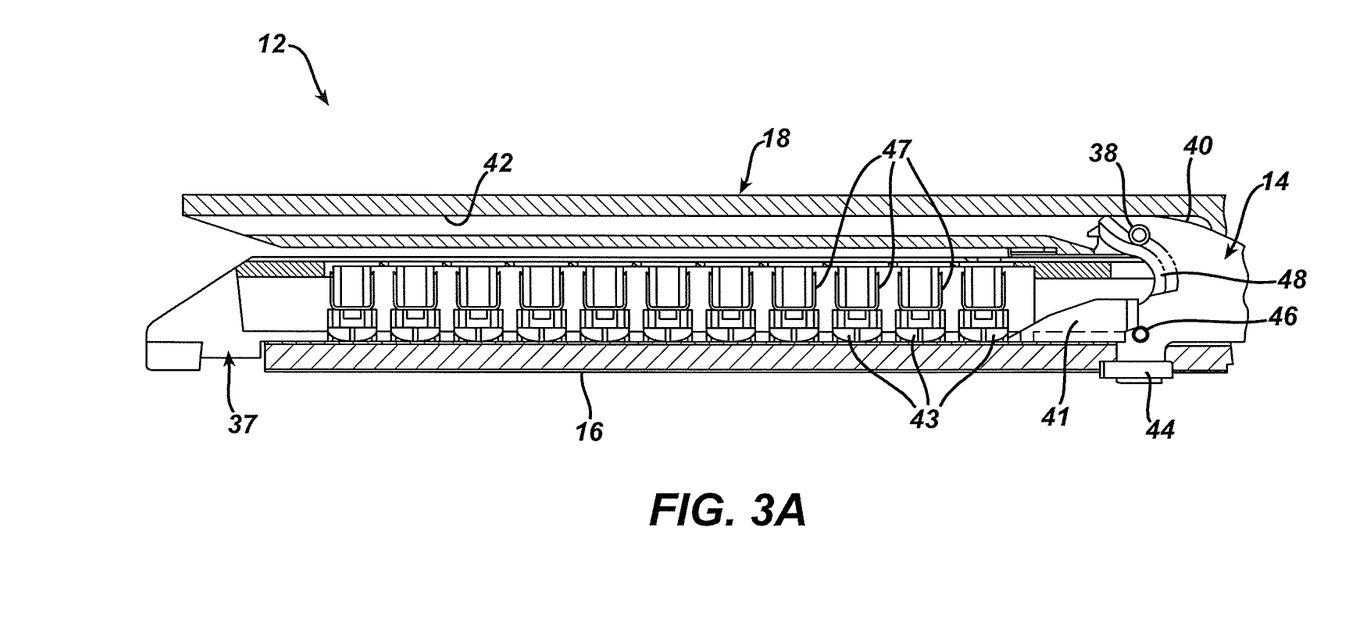
FIG. 3A depicts a side cross-sectional view of the end effector of FIG. 2, taken along line 3-3 of FIG. 2, with the firing bar in a proximal position.
Figure 3B:
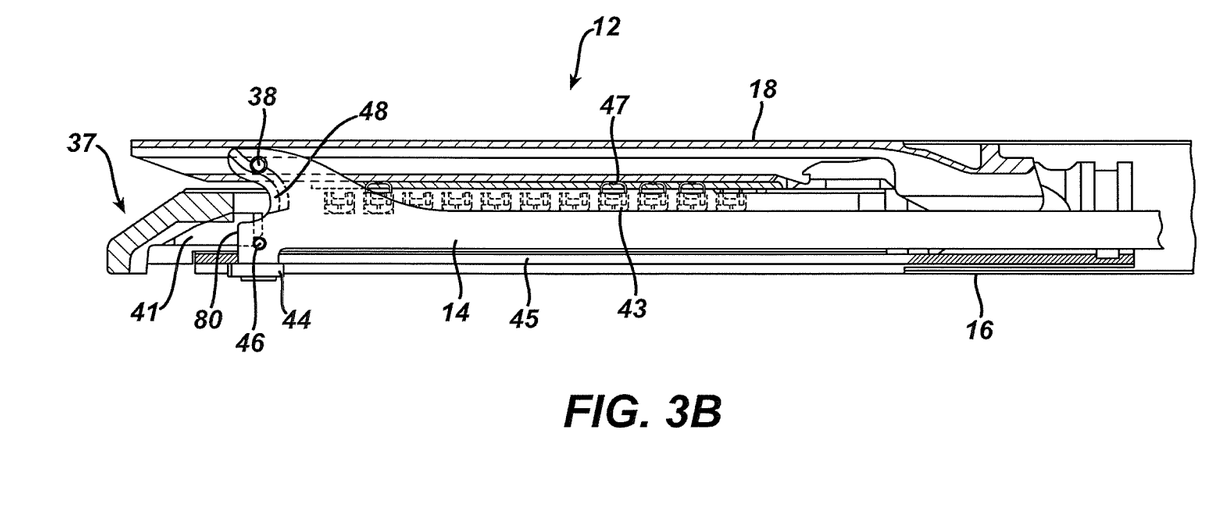
FIG. 3B depicts a side cross-sectional view of the end effector of FIG. 2, taken along line 3-3 of FIG. 2, but showing the firing bar in a distal position.
Figure 4:
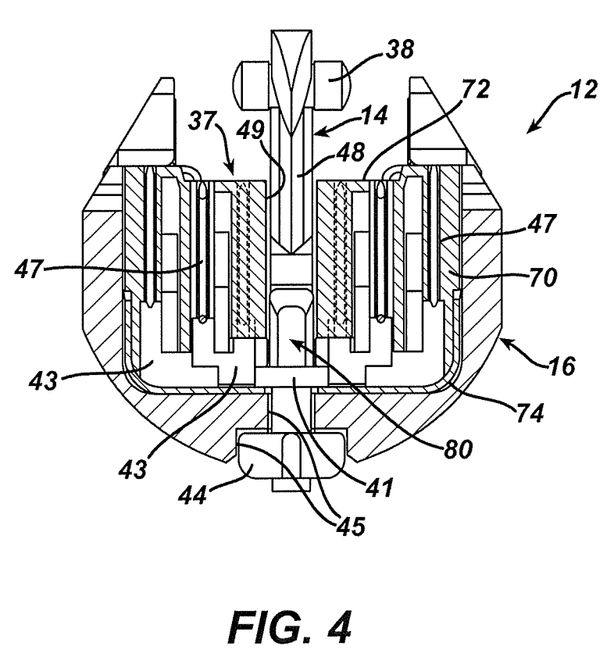
FIG. 4 depicts an end cross-sectional view of the end effector of FIG. 2, taken along line 4-4 of FIG. 2.
Figure 5:
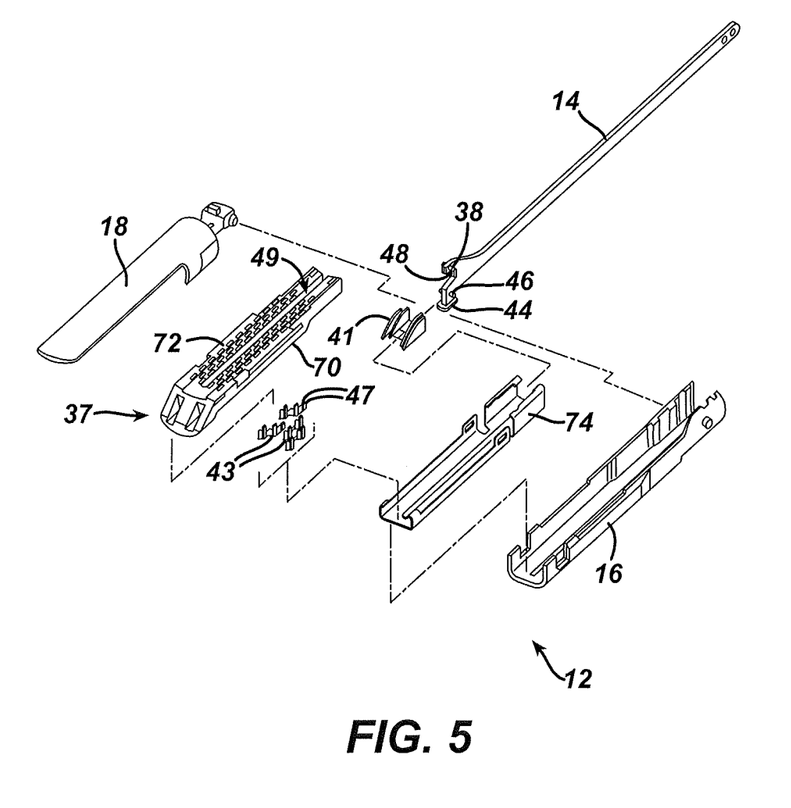
FIG. 5 depicts an exploded perspective view of the end effector of FIG. 2.

FIG. 2 shows firing bar (14) proximally positioned and anvil (18) pivoted to an open position, allowing an unspent staple cartridge (37) to be removably installed into a channel of lower jaw (16). As best seen in FIGS. 4-5, staple cartridge (37) of this example includes a cartridge body (70), which presents an upper deck (72) and is coupled with a lower cartridge tray (74). As best seen in FIG. 2, a vertical slot (49) is formed through part of staple cartridge (37). As also best seen in FIG. 2, three rows of staple apertures (51) are formed through upper deck (70) on one side of vertical slot (49), with another set of three rows of staple apertures (51) being formed through upper deck (70) on the other side of vertical slot (49). Referring back to FIGS. 3-5, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 3A-3B and 5, wedge sled (41) presents inclined cam surfaces that urge staple drivers (43) upwardly as wedge sled (41) is driven distally through staple cartridge (37).

With end effector (12) closed as depicted in FIG. 3A, firing bar (14) is advanced in engagement with anvil (18) by having upper pin (38) enter a longitudinal anvil slot (42). A pusher block (80) is located at the distal end of firing bar (14), and is configured to engage wedge sled (41) such that wedge sled (41) is pushed distally by pusher block (80) as firing bar (14) is advanced distally through staple cartridge (37). During such firing, cutting edge (48) of firing bar (14) enters vertical slot (49) of staple cartridge (37), severing tissue clamped between staple cartridge (37) and anvil (18). As shown in FIGS. 3A-3B, middle pin (46) and pusher block (80) together actuate staple cartridge (37) by entering into a firing slot within staple cartridge (37), driving wedge sled (41) into upward camming contact with staple drivers (43) that in turn drive staples (47) out through staple apertures (51) and into forming contact with staple forming pockets (53) on the inner surface of anvil (18). FIG. 3B depicts firing bar (14) fully distally translated after completing severing and stapling tissue.

Figure 6:
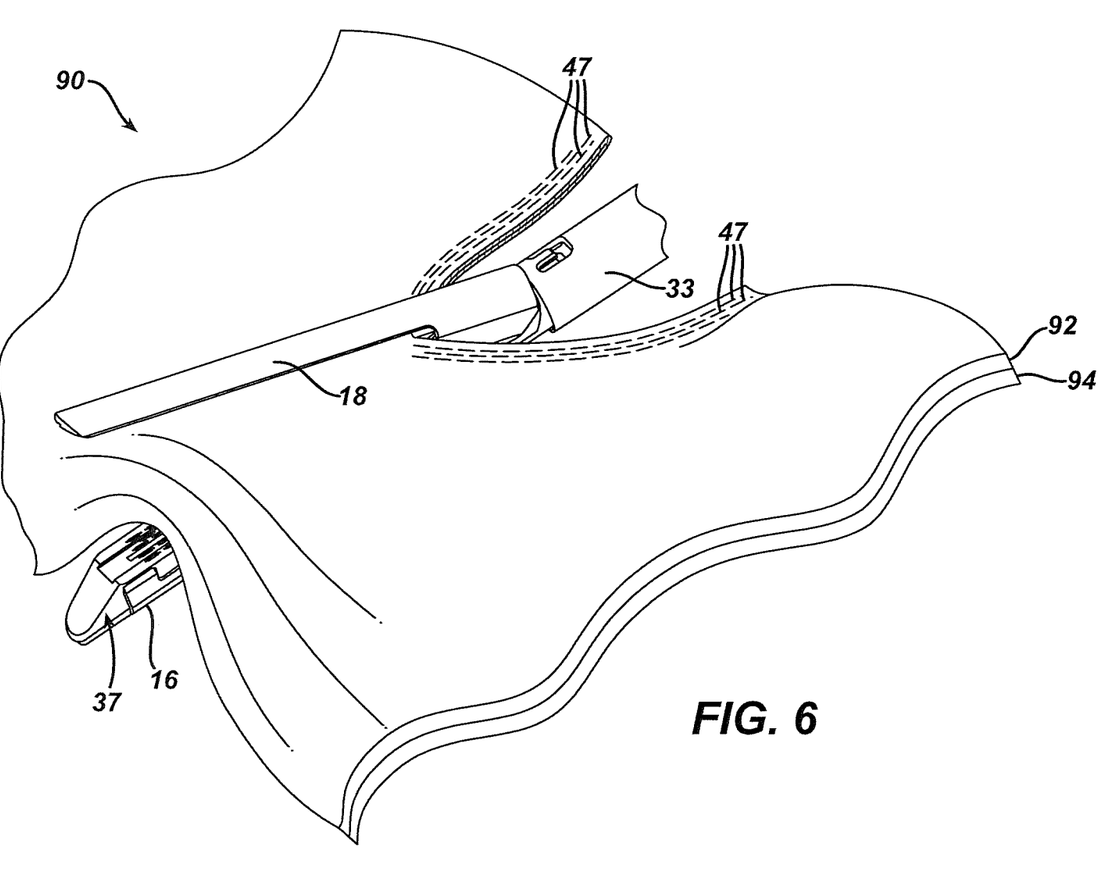
FIG. 6 depicts a perspective view of the end effector of FIG. 2, positioned at tissue and having been actuated once in the tissue.

FIG. 6 shows end effector (12) having been actuated through a single stroke through tissue (90). As shown, cutting edge (48) has cut through tissue (90), while staple drivers (43)

have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 6 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Various suitable settings and procedures in which instrument (10) may be used will be apparent to those of ordinary skill in the art in view of the teachings herein.

It should be understood that instrument (10) may be configured and operable in accordance with any of the teachings of U.S. Pat. No. 4,805,823; U.S. Pat. No. 5,415,334; U.S. Pat. No. 5,465,895; U.S. Pat. No. 5,597,107; U.S. Pat. No. 5,632,432; U.S. Pat. No. 5,673,840; U.S. Pat. No. 5,704,534; U.S. Pat. No. 5,814,055; U.S. Pat. No. 6,964,363; U.S. Pat. No. 6,978,921; U.S. Pat. No. 6,988,649; U.S. Pat. No. 7,000,818; U.S. Pat. No. 7,111,769; U.S. Pat. No. 7,143,923; U.S. Pat. No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434,715; U.S. Pat. No. 7,721,930; and/or U.S. Pat. No. 7,455,208. As noted above, the disclosures of each of those patents are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Cartridge and Matrix Assembly

Figure 7:
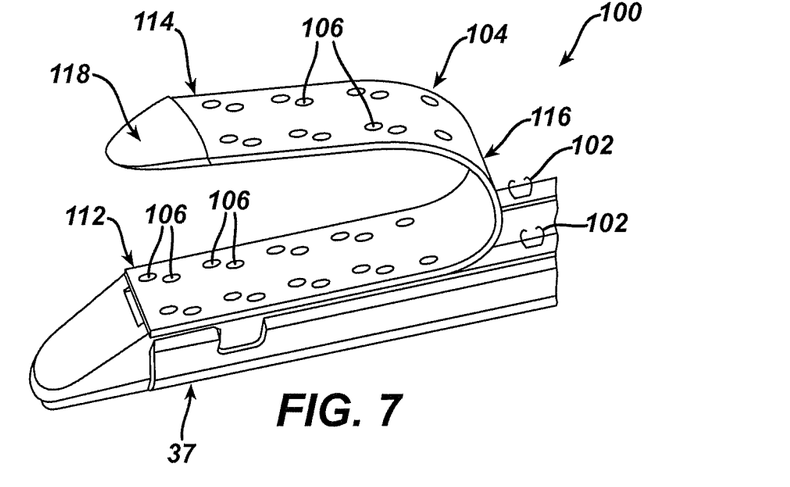
FIG. 7 depicts a perspective, fragmentary view of an exemplary cartridge of the end effector of FIG. 2 and an exemplary fibrin pad matrix disposed above and on an exterior top surface of the cartridge.
Figure 8:
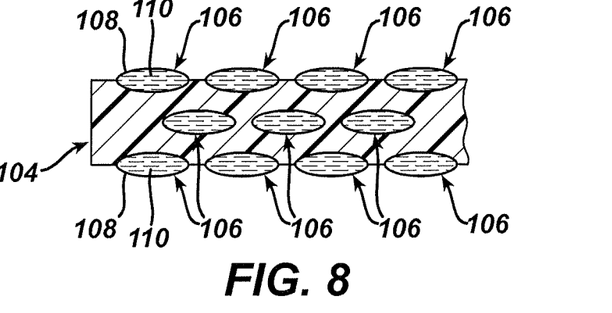
FIG. 8 depicts a cross-sectional view of the fibrin pad matrix of FIG. 7, the matrix including heat activated suspended glue beads.

FIG. 7 shows an exemplary cartridge and matrix assembly (100) in which cartridge (37) includes fasteners such as hooks (102) that grasp onto buttress or matrix (104). Hooks (102) and matrix (104) may provide a fastening relationship, such as a hook and loop fastening relationship in which hooks (102) connect to loops formed within the material of matrix (104). Matrix (104) may be, for example, a fibrin pad matrix including suspended heat activated glue beads (106). As shown in FIG. 8, glue beads (106) are suspended in fibrin pad matrix (104). Each glue bead (106) includes a housing (108) that is thermosensitive to release glue (110) after initial activation with tissue (90) that has a body temperature measurement. Glue bead (106) is heated to a temperature sufficient to initiate activation as glue bead (106) is heated via exposure to the body temperature, for example. In addition or in the alternative, glue beads (106) may be activated by bodily fluids at the surgical site. Glue beads (106) are positioned substantially over staples (47) such that when staples (47) are driven into tissue (90), staples (47) will drive through glue beads (47) and deliver the material to tissue (90). Staples (47) may be made from a material selected from iron, nickel titanium alloy, stainless steel, and/or titanium. Of course, any other suitable materials may be used.

Figure 9:
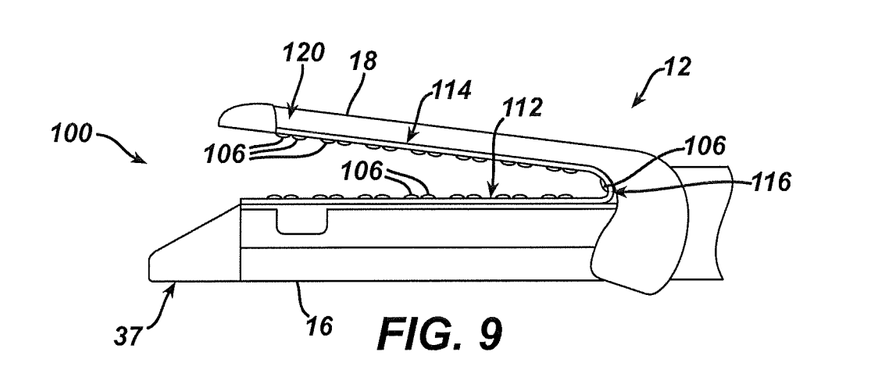
FIG. 9 depicts an elevational view of the end effector of FIG. 2 and the fibrin pad matrix of FIG. 7 disposed on and between an underside of the anvil and the exterior top surface of the cartridge.

Referring back to FIG. 7, matrix (104) includes cartridge portion (112), anvil portion (114), and intermediate portion (116) disposed therebetween at proximal ends of cartridge portion (112) and anvil portion (114). Anvil portion (114) includes flap (118) that wraps over top surface (120) of anvil (18), as shown in FIG. 9. Flap (118), for example, defines a pocket (not shown) sized for receipt of the distal end of anvil (18), to thereby attach anvil portion (114) of matrix (104) to anvil (18). Intermediate portion (116) of matrix (104) may comprise a preformed bend to facilitate loading of cartridge (37) in lower jaw and insertion of anvil (18) in the pocket defined by flap (118).

Figure 10:
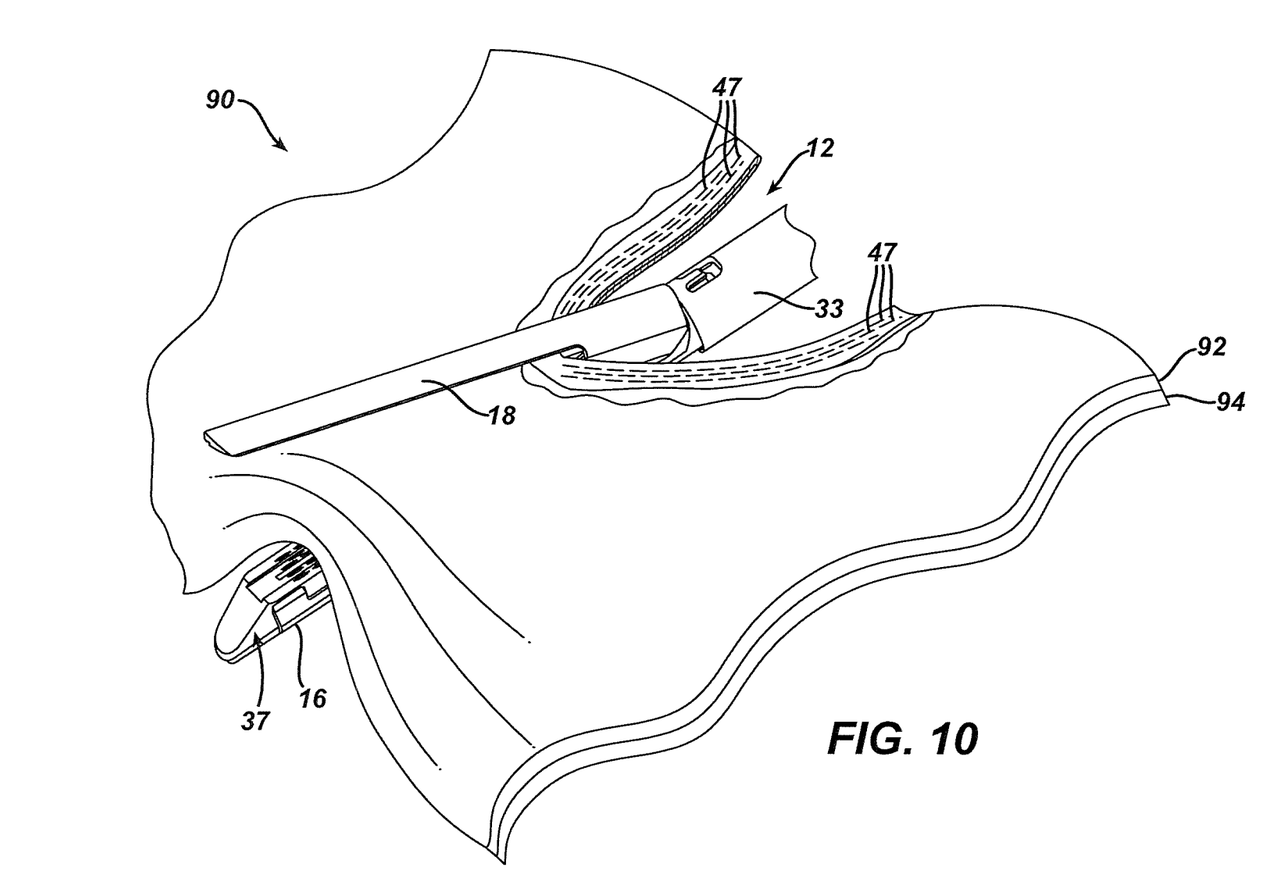
FIG. 10 depicts a perspective view of an end effector with the matrix of FIG. 9, the end effector positioned at and actuated within the tissue to release a tissue repair composition from the buttress and adhesive from the glue beads onto the tissue.

In use, cartridge (37) with matrix (104) is removably received into lower jaw (16) of end effector (12), as shown in FIG. 9. When end effector (12) including cartridge (37) and matrix (104) is used, as shown in FIG. 10, staples (47) are driven into tissue (90) concurrently or slightly prior to firing bar (14) firing into tissue (90) while slicing through matrix (104). Thus, glue beads (106) are driven into tissue (90) via the firing of staples (47) into tissue (90). Staples (47) capture the glue beads and deliver the material to tissue (90), as described above. Additionally, staples (47) may capture portions of fibrin pad matrix (104) and drive those portions into tissue (90) or at least secure fibrin pad matrix (104) to tissue (90). Firing bar (14) slices through matrix (104) as it severs tissue (90) in use, applying material from matrix (104) onto severed tissue. The material forming matrix (104) may comprise a biodegradable polymer operable to assist with tissue repair, for example, as described below. Material severed by firing bar (14) may be deposited onto tissue (90) slightly after material from glue beads (106) is deposited onto tissue (90). As it may take time for the heat from tissue (90) to sufficiently heat and activate glue beads (106) to release glue (110) from housing (108), glue (110) initially released from glue beads (106) is substantially prevented from attaching to and restricting motion of firing bar (14) when firing bar (14) slices through matrix (104).

When surgical staple (47) is driven into tissue by a surgical instrument, such as by instrument (10) in the manner disclosed above, surgical staple (47) will compress, connect, and retain layers of such tissue as shown in FIG. 10. Glue (108) from glue beads (106) will contact the compressed and retained tissue and may be released onto the tissue to assist with tissue repair, such as by acting as an adhesive to seal the tissue together, concurrently assisting to reduce the amount of bleeding at the surgical site.

The material for matrix (104) may comprise, other than fibrin, for example, other adjuncts or hemostatic agents such as thrombin that may assist to coagulate blood and reduce the amount of bleeding at the surgical site. The hemostatic abilities of such adjuncts may also contribute to the use of such adjuncts as adhesives and sealants. The agents may assist to coagulate blood at a surgical site which allows tissue surrounding such blood to stick together and may prevent leaks along the stapled tissue site, for example. Other adjuncts or reagents that may be incorporated into matrix (104) and/or glue beads (106) may further include but are not limited to medical fluid or matrix components. By way of example only, matrix (104) and/or glue beads (106) may include natural or genetically engineered absorbable polymers or synthetic absorbable polymers, or mixtures thereof. Merely illustrative examples of natural or genetically engineered absorbable polymers are proteins, polysaccharides and combinations thereof. Merely illustrative examples of proteins that may be used include prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin, vasopressin analogs, epinephrine, selectin, procoagulant venom, plasminogen activator inhibitor, platelet activating agents, synthetic peptides having hemostatic activity, and/or combinations thereof. Polysaccharides include, without limitation, cellulose, alkyl cellulose, e.g. methylcellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid polygluronic acid, and derivatives of any of the above. Examples of synthetic absorbable polymers are aliphatic polyester polymers, copolymers, and/or combinations thereof. The aliphatic polyesters are typically synthesized in a ring opening polymerization of monomers including, but not limited to, lactic acid, lactide (including L-, D-, meso and D, L mixtures), glycolic acid, glycolide, ε-caprolactone, p-dioxanone (1,4-dioxan-2-one), and trimethylene carbonate (1,3-dioxan-2-one). Other suitable compounds, materials, substances, etc., that may be used in a medical fluid or matrix will be apparent to those of ordinary skill in the art in view of the teachings herein.

In some versions, a medical fluid may be suspended in a biocompatible carrier. Suitable carriers may include, for example, a physiological buffer solution, a flowable gel solution, saline, and water. In the case of gel solutions, the tissue repair composition may be in a flowable gel form prior to delivery at the target site, or may form a gel and remain in place after delivery at the target site. Flowable gel solutions may comprise one or more gelling materials with or without added water, saline, or a physiological buffer solution. Exemplary gelling materials include proteins, polysaccharides, polynucleotides, and other materials such as alginate, crosslinked alginate, poly(N-isopropylacrylamide), poly(oxyalkylene), copolymers of poly(ethylene oxide)-poly(propylene oxide), poly(vinyl alcohol), polyacrylate, or monostearoyl glycerol co-Succinate/polyethylene glycol (MGSA/PEG) copolymers, and combinations of any of the foregoing.

Matrix (104) may alternatively comprise a fibrous pad, a foam, a mesh, or another structure capable of containing an adhesive or other type of medical fluid. By way of example only, matrix (104) may be constructed in accordance with the teachings of U.S. Patent App. Pub. No. 2009/0120994, entitled "Surgical Fastening Device with Initiator Impregnation of a Matrix or Buttress to Improve Adhesive Application", published May 14, 2009, the disclosure of which is incorporated by reference herein. The matrix may comprise, for example, a biocompatible material that is a buttress, a matrix having a plurality of openings therein, an open or closed cell foam, and/or a fabric pad. The material may include porosities that induce a wicking feature to drawing adhesive into the material and ensure the openings remain clear of the adhesive, allowing tissue growth through the openings after application to tissue. Other suitable materials and compositions that may be used to form matrix (104) will be apparent to those of ordinary skill in the art in view of the teachings herein.

Glue beads (106) may be freeze dried prior to suspension in matrix (104) and may be comprised of an adhesive such as, but not limited to, polymerizable and/or cross-linkable materials such as a cyanoacrylate adhesive. The adhesive, for example, may be a monomeric (including prepolymeric) adhesive composition, a polymeric adhesive composition, or any other compound that can adhere to tissue. In embodiments, the monomer may be a 1,1-disubstituted ethylene monomer, e.g., an alpha-cyanoacrylate. When cross linked or polymerized, the cyanoacrylate can change from a liquid to a solid. Polymerized adhesives for example, can be formulated to be flexible to rigid and could be spongy. If desired, the adhesive can be a single part or dual part adhesive, and/or can contain additives such as alternate compounds. Polymerization of the adhesive can occur from, but is not limited to, exposure to moisture, heat, and/or adhesion initiators such as those described in U.S. Patent App. Pub. No. 2009/0120994, the disclosure of which is incorporated by reference above. Other suitable materials and compositions that may be used to form glue bead (106) will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a handle portion;
   (b) a shaft housing a firing bar;
   (c) an end effector comprising an anvil, a lower jaw, and a stapling and severing assembly responsive to a longitudinal closing motion produced by the handle portion and the shaft; and
   (d) a cartridge, wherein the lower jaw is configured to receive the cartridge when the end effector is in an open position, wherein the cartridge comprises:
      (i) a housing,
      (ii) a plurality of staples disposed in the housing,
      (iii) a deck disposed over the plurality of staples, the deck defining apertures, each aperture being substantially disposed over each staple, and
      (iv) a matrix including glue beads suspended in the matrix.

2. The cartridge of claim 1, wherein each glue bead of the glue beads suspended in the matrix comprises glue and a housing, wherein the housing of each glue bead comprises a solid material, wherein the glue is disposed in the solid housing.

3. The cartridge of claim 1, wherein the glue beads suspended are freeze dried.

4. The cartridge of claim 1, wherein the glue beads comprise an adhesive that is selected from the group consisting of the following: polymerizable monomer, a polymerizable 1,1-disubstituted ethylene monomer, and a cyanoacrylate formulation.

5. The cartridge of claim 1, wherein the matrix comprises a biocompatible material.

6. The cartridge of claim 1, wherein the matrix comprises one of fibrin or thrombin.

7. The cartridge of claim 1, wherein each glue bead is substantially disposed over each aperture of the deck.

8. The cartridge of claim 1, wherein the matrix comprises a cartridge portion, an anvil portion, and an intermediate portion disposed therebetween, the anvil portion including a flap which is configured for receipt of a distal end of the anvil.

9. The cartridge of claim 8, wherein the deck of the cartridge includes one or more hooks, wherein the hooks are configured to secure the matrix to the deck of the cartridge.

10. The cartridge of claim 8, wherein the intermediate portion comprises a preformed bend.

11. The cartridge of claim 1, wherein the matrix comprises at least one of a hemostatic agent, a sealant, or an adhesive.

12. The cartridge of claim 1, wherein the staples comprise a material selected from at least one of the following materials: iron, nickel titanium alloy, stainless steel, and titanium.

13. The cartridge of claim 1, wherein the matrix comprises a biocompatible material selected from a group consisting of at least one of the following materials: epsilon-caprolactone glycolide, bovine pericardium, polylactic acid, polyglycolic acid, polyglactin, polydioxanone, polyglyconate, whey protein, cellulose gum, starch, gelatin, silk, nylon, polypropylene, braided polyester, polybutester, polyethylene, and polyetheretherketones.

14. The cartridge of claim 1, wherein the matrix comprises a biocompatible material selected from a group consisting of at least one of the following: a buttress, a matrix having a plurality of openings therein, an open cell foam, a closed cell foam, and a fabric pad.

15. The cartridge of claim 1, wherein the matrix includes at least one wicking feature.

16. A method of releasing and activating adhesive with a surgical instrument, the surgical instrument including an end effector, a handle portion, a shaft, a stapling and severing assembly, a matrix, and a removable cartridge, wherein the end effector comprises a lower jaw and an anvil, the lower jaw being configured to receive a removable cartridge, wherein the stapling and severing assembly is responsive to a longitudinal closing motion produced by the handle portion and the shaft, wherein the matrix includes glue beads suspended in the matrix, wherein the cartridge includes an exterior top surface, wherein a first portion of the matrix is disposed on the exterior top surface of the cartridge, the method comprising the steps of:
   (a) disposing the matrix on the end effector of the surgical instrument between the lower jaw and the anvil;
   (b) activating the stapling and severing assembly to drive staples through the matrix; and
   (c) applying at least one of heat or moisture to the matrix to an amount sufficient to activate the glue beads suspended in the matrix.

17. The method of claim 16, wherein the step of disposing the matrix on the end effector comprises:
   (i) inserting the removable cartridge into the lower jaw, and
   (ii) disposing a second portion of the matrix on an underside of the anvil.

18. The method of claim 16, wherein the step of disposing the matrix on the end effector comprises:
   (i) disposing a first portion of the matrix on the exterior top surface of the cartridge, and
   (ii) attaching the first portion of the matrix to the exterior top surface via a series of hooks extending from the exterior top surface.

19. The method of claim 16, wherein the step of disposing the matrix on the end effector comprises:
   (i) disposing a second portion of the matrix on an underside of the anvil, and (ii) inserting a distal end of the anvil into a flap on the second portion of the matrix, wherein the flap is configured for receipt of the distal end of the anvil.

20. A surgical instrument comprising:
(a) a handle portion;
(b) a shaft, the shaft housing a firing bar;
(c) a stapling and severing assembly responsive to a longitudinal closing motion produced by the handle portion and the shaft;
(d) a staple cartridge, wherein the staple cartridge comprises:
 (i) a plurality of staples, and
 (ii) a deck disposed over the plurality of staples, the deck defining apertures, each aperture being substantially disposed over at least one respective staple;
(e) an end effector connected to the shaft, the end effector comprising an anvil and a lower jaw, the cartridge being received in the lower jaw, the anvil being configured to form the staples in response to a longitudinal closing motion when the end effector is in a closed position; and
(f) a biocompatible material containing glue beads suspended in a matrix, the biocompatible material being releasably attached to the cartridge and the anvil;
wherein the staples are operable to be driven through the biocompatible material.

* * * * *